(12) United States Patent
Nawa et al.

(10) Patent No.: US 6,569,547 B2
(45) Date of Patent: May 27, 2003

(54) HARD TISSUE REPAIRING MATERIALS AND THE PROCESS FOR PRODUCING THE SAME

(75) Inventors: Masahiro Nawa, Katano (JP); Tadashi Kokubo, 50, Umegaoka 2-chome, Nagaokakyo-shi Kyoto 617-0841 (JP); Masaki Uchida, Kyoto (JP)

(73) Assignees: Matsushita Electric Works, Ltd., Kadoma (JP); Tadashi Kokubo, Nagaokakyo (JP)

( * ) Notice: Subject to any disclaimer, the term of this patent is extended or adjusted under 35 U.S.C. 154(b) by 0 days.

(21) Appl. No.: 09/969,772

(22) Filed: Oct. 4, 2001

(65) Prior Publication Data

US 2002/0072807 A1 Jun. 13, 2002

(30) Foreign Application Priority Data

Oct. 10, 2000 (JP) ........................................ 2000-308586

(51) Int. Cl.[7] .................................................. B32B 9/00
(52) U.S. Cl. ...................... 428/701; 428/469; 428/697; 428/698; 428/699; 428/701; 623/16.11; 623/23.56; 623/23.57; 623/23.58; 623/23.6; 427/2.26; 427/372.2
(58) Field of Search ......................... 428/469, 697–699, 428/701–702; 623/16.11, 23.56, 23.58, 23.6; 501/102; 427/2.1, 2.24, 2.26, 372.2

(56) References Cited

FOREIGN PATENT DOCUMENTS

| EP | 0348288 | * 12/1989 | ........... C23C/18/12 |
|----|---------|-----------|----------------------|
| JP | 6-23030 | 2/1994 | |
| JP | 10-179718 | 7/1998 | |

OTHER PUBLICATIONS

M. Uchida, et al., Bioceramics, vol. 11, pp. 77–80, "Apatite–Forming Ability of Zirconia Gel in Modified SBF Solutions," Nov. 1998.

* cited by examiner

Primary Examiner—Deborah Jones
Assistant Examiner—Arden B. Sperty
(74) Attorney, Agent, or Firm—Oblon, Spivak, McClelland, Maier & Neustadt, P.C.

(57) ABSTRACT

A hard tissue repairing material including a base material and a surface layer having a crystalline zirconia covering the base material, being characterized in that the film includes a Zr—OH group. A middle layer may be formed between the base material and the surface layer and, in such case, includes at least one element of the base material and at least one element of the surface layer having a crystalline zirconia.

17 Claims, No Drawings

HARD TISSUE REPAIRING MATERIALS AND THE PROCESS FOR PRODUCING THE SAME

BACKGROUND OF THE INVENTION

1. Field of the Invention

The present invention relates to hard tissue repairing materials and, particularly, to a bone repairing material that is used to repair when articular function and/or bone function of hands and feet are lost. Furthermore, the invention relates to an implant that can be used as an artificial tooth, for rebuilding the teeth and tusks when the teeth had been lost because of senility or illness.

2. Description of the Prior Art

In the case of damage in a hard tissue repairing material, e.g., a bone and a tooth, any artificial hard tissue repairing materials may be inserted in living body for treatment. The hard tissue repairing material has to be bonded to the living hard tissue in living body after having been inserted. In order to bond the hard tissue repairing material to a living hard tissue, the hard tissue repairing material should have any functional group capable of inducing the nucleation of hydroxyapatite so that hard tissue repairing material should have a "bone-like apatite" on its surface. The bone-like apatite is the hydroxyapatite which has carbonate ion ($CO_3^{2-}$) and low Ca ion concentration (Ca deficiting) regarding with stoichiometric composition ($Ca_{10}(PO_4)_6(OH)_2$). The bone-like apatite also has a Ca/P ratio that is lower than 1.67 of the stoichiometric hydroxyapatite. The bone-like apatite has a plurality of lattice defect and is constructed by fine particles. Therefore, the bone-like apatite is nearly equal to the bone apatite of living bone.

It is known that a hard tissue repairing material including a base material, e.g., metal or ceramics, and a zirconia gel layer made by a sol-gel process. The zirconia gel layer has a Zr—OH group that may induce a nucleation of apatite. (See, Bioceramics volume 11 Ed. by R. Z. LeGros and J. P. LeGros, World Scientific, (1998) pp77–80).

By the way, several prior art methods of giving the bioactive function at the surface of a base material are disclosed in some literature. For example, the Japanese Laid-open Patent Publication No. 6-23030 discloses a method of forming a coating layer of silica gel or titania gel on the surface of a base material. The Japanese Laid-open Patent Publication No. 10-179718 discloses a method of improving the surface of a base material of titanium metal and titanium alloys to bioactive by soaking in an alkaline fluid.

The layer having the hydroxyl group formed by the method of the Japanese Laid-open Patent Publication No. 6-23030 is a silica gel layer or a titania gel layer on the surface of the base materials. Similarly, the bioactive layer formed by the method of the Japanese Laid-open Patent Publication No. 10-179718 is titania phase, titania gel phase, alkaline-titanate phase, and alkaline-titanate gel phase However, the prior art hard tissue repairing material has a low level ability of inducing the nucleation of hydroxyapatite and, accordingly, the prior art hard tissue repairing material can not be bonded greatly to a living hard tissue in living body.

SUMMARY OF THE INVENTION

Therefore, it is an object of the present invention to provide a hard tissue repairing material having a high bioactivity.

In accordance with one aspect of the present invention, there is provided a hard tissue repairing material including a base material and a surface layer having a crystalline zirconia covering the base material, which the surface layer includes a Zr—OH group.

The hard tissue repairing material includes a surface layer having a Zr—OH group to induce a nucleation of apatite. Additionally, the hard tissue repairing material of this invention can form large amount of apatite, so that the hard tissue repairing material may have a good bioactivity. We consider that the hard tissue repairing material includes a surface layer having the crystalline zirconia so that the apatite can grow as maintaining the coordination between the crystalline direction of the Zr—OH group and the crystalline direction of the OH group of apatite. The surface layer having the crystalline zirconia may have a thickness ranging from 0.5 to 50 μm, preferably thickness ranging from 1 to 10 μm, more preferably thickness ranging from 1 to 5 μm.

Preferably, a middle layer between the base material and the surface layer, which includes at least one element of the base material and at least one element of the surface layer having a crystalline zirconia, may be formed. With the middle layer, the contact between the base material and the surface layer having the crystalline zirconia can have a good contact strength. The middle layer may include an amorphous phase or crystal phase. Additionally, the middle layer may include a composite, e.g., double salt, or solid solution including at least two elements.

The surface layer may have a tetragonal zirconia, a monoclinic zirconia, or the both. Preferably, the surface layer may contain at least an ionic component that is selected from the group consisting of calcium ion, sodium ion, potassium ion, and phosphate ions. Consequently, the ionic component within the surface layer can promote a bone-like apatite. More preferably, the hard tissue repairing material may further include a second layer containing an apatite layer as a main component formed on the surface layer having the crystalline zirconia. The apatite layer in the second layer can promote the apatite spontaneously in the living body.

The base material may be a ceramic material including an oxide group, a carbide group, a nitride group, or a boride group. Additionally, e.g., silica-glass, preferably zirconia, zirconia-alumina composite may be used. The base material may be a metal material, e.g., titanium, Co—Cr—Mo alloy, and may be a polymer material.

A process for producing a hard tissue repairing material includes preparing a base material, coating the base material with a zirconia sol, and crystallizing the zirconia sol.

The zirconia sol solution may include zirconium alkoxide, alcohol, distilled water, acid catalyst. Preferably, a solution including $Zr(OC_3H_7)_4$, $C_2H_5OH$, $H_2O$ and $HNO_3$ may be used as zirconium sol solution. Soaking the base material in the zirconia sol solution may result in coating of the base material with the zirconia sol. Additionally, crystallizing the zirconia sol may be effected by heating. It is noted that coating the zirconia sol and heating the base material having the zirconia sol on the surface may be repeated. According to desired repeats of coating and heating, the surface layer having the crystalline zirconia may have a thickness ranging from 0.5 μm to 50 μm, preferably from 1 μm to 10 μm, and more preferably from 1 μm to 5 μm.

The heating temperature is not limited, provided that the crystalline zirconia can be formed by heating. The temperature will be dependent on any conditions, e.g., the composition of the zirconia sol solution and/or the atmosphere. In the case that the zirconia sol solution including $Zr(OC_3H_7)_4$, $C_2H_5OH$, $H_2O$ and $HNO_3$ is used, the base material having the zirconia sol on the surface may be heated at not lower than 500° C. in air. More preferably, the base material may be heated at not higher than 800° C. If the base material is heated under other condition, e.g., in a hydrothermal bath, the base material may be heated at much lower than 500° C.

A process for producing a hard tissue repairing material includes preparing a base material, coating the base material with a zirconia sol, heating the base material having the zirconia sol on the surface. Then, the diffusing layer having at least an element of the base material and at least an element of the zirconia sol is formed on the base material. Subsequently, coating the diffusing layer with a zirconia sol, and crystallizing the zirconia sol on the diffusing layer. Therefore, the surface layer having a crystalline zirconia is formed, and a middle layer between the base material and the surface layer is formed by the diffusion layer.

The heating condition to form the middle layer is not limited, provided that the element can diffuse. The heating condition may be changeable according to the base material. For example, where the ceramic material, e.g., silica-glass, zirconia, zirconia-alumina composite is used as base material, the base material having the zirconia gel on the surface may be heated at not lower than 1000° C. If the metal, e.g., titanium, is used as base material, the base material may be heated within an inert gas, e.g., $N_2$, Ar gas in order to prevent the oxidation. Additionally, the base material may be heated at not higher than 800° C. in order to prevent the phase transition from alpha phase to beta phase.

The base material may include a hydrophilic group, e.g., a hydroxyl group. According to the hydrophilic group of the base material, the surface layer can have a good contact strength to the base material, because the hydrophilic group of the base material may be bonded to the hydroxyl group of the surface layer by dehydration and condensation. The base material may be soaked in an alkaline aqueous solution or an acid aqueous solution after the step of preparing the base material to provide a hydrophilic group on the surface.

Preferably, the zirconia sol may include at least an ionic component selected from the group consisting of calcium ion, sodium ion, potassium ion, and phosphate ions so that the surface layer may include the ionic component. In order to include the ionic component in the zirconia sol, a compound having the desired ion may be added in the zirconia sol solution. The compound may be a metallic hydroxide, e.g., calcium hydroxide, sodium hydroxide, potassium hydroxide, and an alkoxide, e.g., calcium ethoxide, sodium ethoxide, potassium ethoxide, and a nitrate, e.g., sodium nitrate, calcium nitrate, potassium nitrate, and acetate, carbonate, chloride, phosphate.

After crystallizing the zirconia sol, the process for producing a hard tissue repairing material may further include the step of soaking the base material in a molten salt containing at least an ionic component selected from the group consisting of calcium ion, sodium ion, potassium ion, and phosphate ions.

After crystallizing the zirconia sol, the process for producing a hard tissue repairing material may further include the step of soaking the base material in an aqueous solution containing at least an ionic component selected from the group consisting of calcium ion, sodium ion, potassium ion, and phosphate ions.

A process for producing a hard tissue repairing material may further include the last step of soaking the base material including the surface layer having the crystalline zirconia in the simulated body fluid with ion concentrations nearly equal to those of human body fluid. The simulated body fluid (called "SBF" hereunder) may be, e.g., the solution including $Na^+$ 142 mM, $K^+$ 5.0 mM, $Mg^{2+}$ 1.5 mM, $Ca^{2+}$ 2.5 mM, $Cl^-$ 147.8 mM, $HCO_3^-$ 4.2 mM, $HPO_4^{2-}$ 1.0 mM, $SO_4^{2-}$ 0.5 mM.

According to the hard tissue repairing material of this invention, it has a surface layer having the crystalline zirconia to form apatite layer. Therefore, the hard tissue repairing material can have a good bioactivity. Additionally, according to the process for producing the hard tissue repairing material of this invention, the hard tissue repairing material having a good bioactivity can be provided.

DETAILED DESCRIPTION OF THE PREFERRED EMBODIMENTS

EXAMPLE 1

In the first example, a zirconia sol solution No. 1 including $Zr(OC_3H_7)_4$, $C_2H_5OH$, $H_2O$ and $HNO_3$ was prepared. The molecular ratio $Zr(OC_3H_7)_4:C_2H_5OH:H_2O:HNO_3$ is 1.0:25.0:1.0:0.1. Subsequently, several silica-glass base materials, zirconia base materials, and titanium base materials were prepared. Each base material had a size of 10 mm by 10 mm by 1 mm. Then, every base material was soaked in the zirconia sol solution No. 1 and withdrawn to coat the zirconia sol solution No. 1 on its surface. The base materials were heated at 400° C., 600° C., or 800° C. in air for 10 minutes. Additionally, coating the base materials with the zirconia sol solution No. 1 and heating the base materials were repeated five times under same conditions. Consequently, the hard tissue repairing materials having a surface layer including the zirconia were provided. The surface layer including zirconia was analyzed with respect to crystal structure by a thin film X-ray diffraction method (TF-XRD). As a result, it is found that the surface layer heated at 400° C. is amorphous, the surface layer heated at 600° C. is tetragonal phase, and the surface layer heated at 800° C. is mixture of tetragonal phase and monoclinic phase regardless of the species of base material. The base materials were analyzed with 1 s orbital electron of oxygen by X-ray photo-electron spectroscopy (XPS). Then, the spectrum of 1 s orbital electron of oxygen in XPS data were separated into Zr—O—Zr bonding, Zr—OH bonding, and adsorbed water. As a result, it is found that every base material had the surface layer including the Zr—OH group.

The base materials were soaked in the simulated body fluid. The simulated body fluid included $Na^+$ 142.0 mM, $K^+$ 5.0 mM, $Ca^{2+}$ 2.5 mM, $Mg^{2+}$ 1.5 mM, $Cl^-$ 147.8 mM, $HCO_3^-$ 4.2 mM, $HPO_4^{2-}$ 1.0 mM, $SO_4^{2-}$ 0.5 mM and was adjusted to pH 7.40 at 36.5° C. After the soaking the base material in the simulated body fluid, the base materials were taken out seven days later and fourteen days later. Then, the base materials were analyzed with respect to the apatite deposition on the surface by scanning electron microscopy (SEM). The results are shown in Tables 1 to 3.

TABLE 1

The amount of apatite deposition on the surface of the silica-glass base materials

| heating temperature (° C.) | crystal structure of the surface layer | the amount of apatite deposition 7 days later | 14 days later |
|---|---|---|---|
| 400 | amorphous | X | Δ |
| 600 | tetragonal phase | ○ | ⊙ |
| 800 | mixture of tetragonal phase and monoclinic phase | ○ | ⊙ |

X: no deposition;
Δ: a little layer deposited as dot pattern;
○: deposited on the whole surface; and
⊙: deposited as layer on the whole surface.

TABLE 2

The amount of apatite deposition on the surface of the zirconia base materials

| heating temperature (° C.) | crystal structure of the surface layer | the amount of apatite deposition 7 days later | 14 days later |
|---|---|---|---|
| 400 | amorphous | X | Δ |
| 600 | tetragonal phase | ○ | ⊙ |
| 800 | mixture of tetragonal phase and monoclinic phase | ○ | ⊙ |

X: no deposition;
Δ: a little layer deposited as dot pattern;
○: deposited on the whole surface; and
⊙: deposited as layer on the whole surface.

TABLE 3

The amount of apatite deposition on the surface of the titanium base materials

| heating temperature (° C.) | crystal structure of the surface layer | the amount of apatite deposition 7 days later | 14 days later |
|---|---|---|---|
| 400 | amorphous | X | Δ |
| 600 | tetragonal phase | ○ | ⊙ |
| 800 | mixture of tetragonal phase and monoclinic phase | ○ | ⊙ |

X: no deposition;
Δ: a little layer deposited as dot pattern;
○: deposited on the whole surface; and
⊙: deposited as layer on the whole surface.

Referring to the Tables 1 to 3, it is found that any hard tissue repairing material had the apatite deposition 14 days later. As compared with the crystal structure of the surface layer, however, the hard tissue repairing material having the surface layer including the tetragonal phase or mixture of tetragonal phase and monoclinic phase had much amount of apatite deposition than including the amorphous phase.

EXAMPLE 2

In the second example, adding a calcium nitride and phosphate salt in the zirconia sol solution No. 1 in Example 1 to prepare a zirconia sol solution No. 2. The molecular ratio in the zirconia sol solution No. 2 was Zr:Ca:P=1:1:1. Subsequently, several zirconia base materials having a size of 10 mm by 10 mm by 1 mm were prepared. The zirconia base materials included a first phase of tetragonal zirconia polycrystal in 70 volume % and a second phase of zirconia-alumina composite in 30 volume %. The zirconia base material was a sintered composite material so that the first and second phases were dispersed in each other. The first phase of tetragonal zirconia polycrystals were stabilized with 10 mol % of ceria as a stabilizing agent.

The base materials were soaked in the zirconia sol solution No. 2. Then the base materials were taken out to be coated with the zirconia sol solution No. 2 on the surface. The base materials were heated at 1200° C. for 30 minutes in air. Subsequently, the base materials were coated with zirconia sol solution No. 2 in the foregoing condition. The base materials were heated at 1100° C. for 30 minutes. The base materials were coated with the zirconia sol solution No. 2 again, and heated at 800° C. for 10 minutes. Then, the base materials were coated with the zirconia sol solution No. 1, and heated at 800° C. The coating and heating were repeated 5 times in total. Therefore, the hard tissue repairing materials having the surface layer including zirconia were provided. The thickness of the surface layer may be within the ranging from 2 μm to 3 μm.

The cross section of the surface layer of the hard tissue repairing material was analyzed by an energy dispersive X-ray analysis (EDAX) and, as a result, the element of Ca, Zr, P, O, Ce were detected. Therefore, it is found that the element of Ce was diffused from the base material to the surface layer and the element of Zr was diffused from the surface layer to the base material. As a result, it is confirmed that a middle layer between the base material and the surface layer formed by at least one element of the base material and at least one element of the surface layer. The surface layer was analyzed with respect to crystal structure by thin film X-ray diffraction method (TF-XRD) every heating treatment. As a result, any diffraction peak due to a phosphate composite salt $CaZr_4(PO_4)_6$ was detected in the surface of the base materials heated at 1200° C., 1100° C., 1000° C. Therefore, according to the result of energy dispersive X-ray analysis (EDAX) and thin film X-ray diffraction method (TF-XRD), it is assumed that the phosphate composite salt $CaZr_4(PO_4)_6$ may form a solid solution $CaZr_{4-x}Ce_x(PO_4)_6$, at which the $Ce^{4+}$ ion of the base material origin is substituted for $Zr^{4+}$ ion. It is found that the hard tissue repairing material had a last external surface layer formed by tetragonal zirconia and/or monoclinic zirconia. However, any diffraction peak due to the phosphate composite salt $CaZr_4(PO_4)_6$ could not be detected on the surface of the last external surface layer. Additionally, the base materials were analyzed with 1 s orbital electron of oxygen by X-ray photo-electron spectroscopy (XPS). As a result, it is found that every base material had the external surface layer including the Zr—OH group as the first embodiment.

The hard tissue repairing materials were soaked in 30 ml of the simulated body fluid (SBF) as was in Example 1. Then, the hard tissue repairing materials were taken out fourteen days later, 100 square pieces were marked as matrix of 10 by 10 on the surface of the hard tissue repairing materials. An adhesive tape was stuck on every square piece, then the tape was peeled from the surface of the hard tissue repairing material. Therefore, the number of exfoliation piece of the surface layer from the surface was counted to evaluate the contact strength between the base material and the surface layer. Notes that the three hard tissue repairing materials of the first embodiment were evaluated for contact strength by above method.

Consequently, 5 to 20 pieces were exfoliated from the surface in Example 1. By the way, not more than 5 pieces may be exfoliated from the surface in Example 2. Therefore, it is found that the contact strength between the base material and the surface layer may increase due to the diffusion of the element between the base material and the surface layer.

EXAMPLE 3

In this Example 3, sodium ethoxide ($C_2H_5ONa$), potassium ethoxide or phosphate salt were added in the zirconia sol solution No. 1 in Example 1, so that three species of the zirconia sol solution No. 3 to 5 were prepared respectively. The molecular ratio of the zirconia sol solution No. 3 to 5 were Zr:Na=1:0.2, Zr:K=1:0.2 and Zr:P=1:0.2 respectively. Then, several silica-glass base materials, zirconia base materials and titanium base materials were prepared. Each base material was 10 mm by 10 mm by 1 mm in size. The base materials were soaked in the zirconia sol solution No. 3 to 5 to be coated with the sol No. 3 to 5 respectively. Subsequently, the base materials were heated at 600° C. for 10 minutes in air. The soaking and heating were repeated 5 times in total under the same condition. Therefore, the hard tissue repairing materials having the surface layer including the zirconia were provided.

The surface layer of the hard tissue repairing material was analyzed with respect to crystal structure by the thin film X-ray diffraction method. As a result, it is found that the crystal structure of the surface layer was tetragonal phase and/or monoclinic phase. The spectrum of 1 s orbital electron of oxygen was analyzed by X-ray photo-electron spectroscopy (XPS) as the first embodiment, it is found that each surface layer included Zr—OH group. Additionally, sodium ion, potassium ion and phosphate ion were detected in the surface layer soaked in the sol No. 3 to 5 respectively.

The hard tissue repairing materials were soaked in 30 ml of the simulated body fluid as was in Example 1. The hard tissue repairing materials were taken out 7 days later, and were analyzed with respect to the amount of apatite deposition by a scanning electron microscope to compare with the tables 1 to 3 of Example 1.

Resultantly, in Example 3, each hard tissue repairing material had apatite layer deposited on the whole surface of the surface layer. The apatite layer was as much as the base material soaked for 14 days in Example 1. Therefore, it is found that apatite formation can be promoted due to sodium ion, potassium ion or phosphate ion in the surface layer.

EXAMPLE 4

In this Example 4, several silica-glass base materials, zirconia base materials and titanium base materials were prepared. Each base material had a size of 10 mm by 10 mm by 1 mm. The silica-glass base materials were soaked in 5 ml of 10 mol/l potassium hydroxide solution holding at 60° C. for 1 day. The zirconia base materials were soaked in 5 ml of 5 mol/l phosphate solution holding at 95° C. for 4 days. The titanium base materials were soaked in 5 ml of 10 mol/l sodium hydroxide solution holding at 60° C. for 1 day. The surface of the base materials were analyzed by thin film X-ray diffraction method. It is found that the surface of each base material had hydroxide group.

The base materials were soaked in the zirconia sol solution No. 1, and were taken out to be coated with the sol solution No. 1. Then, the base materials were heated at 600° C. for 10 minutes in air. The coating and heating were repeated under the same condition 5 times in total. Therefore, the hard tissue repairing materials having the surface layer including the zirconia were provided.

The crystal structure of the surface layer was analyzed by thin film X-ray diffraction method. Then, it is found that the surface layer was tetragonal phase and/or monoclinic phase. The spectrum of 1 s orbital electron of oxygen was analyzed by X-ray photo-electron spectroscopy. It is found that each surface layer included Zr—OH group.

The hard tissue repairing materials were soaked in 30 ml of the simulated body fluid used in Example 1, and were taken out 14 days later. Then the hard tissue repairing materials were evaluated with respect to the contact strength between the base material and the surface layer by the method used in Example 2. Consequently, the number of the exfoliation pieces from the surface may be not more than 5 pieces. Therefore, it is found that the contact strength between the base material and the surface layer may be improved due to the hydroxide group on the surface.

EXAMPLE 5

In this Example 5, several zirconia base materials having the size of 10 mm by 10 mm by 1 mm were prepared. The zirconia base materials were soaked in the zirconia sol solution No. 1 to be coated with the sol solution No. 1. Then the base materials are heated at 800° C. for 10 minutes in air. The coating and heating were repeated under the same condition 5 times. Therefore, the hard tissue repairing materials having the surface layer including the zirconia were provided.

The hard tissue repairing materials were soaked in a chloride molten salt at 580° C. for 1 hour. The chloride molten salt was mixed and melted at 580° C., at which ratio of calcium chloride/sodium chloride was 5:5. Subsequently, the hard tissue repairing materials were soaked in a carbonate molten salt at 850° C. for 1 hour. The carbonate molten salt was mixed and melted at 850° C., at which ratio of calcium carbonate/potassium carbonate was 6:4. The hard tissue repairing materials were cleaned by water, and dried. The surface layer was analyzed by X-ray photo-electron spectroscopy, then the peak due to calcium ion, sodium ion and potassium ion were detected. The crystal structure of the surface layer was analyzed by thin film X-ray diffraction method, then it is found that the surface layer included tetragonal phase and/or monoclinic phase. The spectrum of 1s orbital electron of oxygen was analyzed by X-ray photo-electron spectroscopy as was the case with Example 1. It is found that the surface layer of each hard tissue repairing material included Zr—OH group.

The hard tissue repairing materials were soaked in 30 ml of the simulated body fluid of the first embodiment, and were taken out 7 days later. Then, the amount of the apatite deposition were analyzed by scanning electron microscope to compare with the table 2 in Example 1. Consequently, the apatite layer was deposited on the whole surface, and was as much as the hard tissue repairing material soaked in the simulated body fluid for 14 days as was in Example 1. Therefore, it is found that the apatite formation may be promoted due to calcium ion, sodium ion or potassium ion including in the surface layer.

The present disclosure relates to subject matter contained in priority Japanese Patent Application Nos. 2000-308586, filed on Oct. 10, 2000, and 2001-231891, filed on Jul. 31, 2001, the contents of both of which are herein expressly incorporated by reference in their entireties.

What is claimed is:

1. A hard tissue repairing material comprising:
   a base material; and
   a surface layer formed on a surface of the base material and containing a crystalline zirconia, said surface layer also including a Zr—OH group.

2. The hard tissue repairing material according to claim 1, further including a middle layer between the base material and the surface layer, and wherein the middle layer includes at least one element of the base material and at least one element of the surface layer having a crystalline zirconia.

3. The hard tissue repairing material according to claim 1, wherein said surface layer having at least a crystalline zirconia that is selected from the group consisting of tetragonal zirconia and monoclinic zirconia.

4. The hard tissue repairing material according to claim 1, wherein said base material is ceramic material.

5. The hard tissue repairing material according to claim 1, wherein said base material is zirconia or zirconia-alumina composite.

6. The hard tissue repairing material according to claim 1, wherein said surface layer contains at least an ionic component that is selected from the group consisting of calcium ion, sodium ion, potassium ion, and phosphate ions.

7. The hard tissue repairing material according to claim 1, further including a second layer containing an apatite layer as a main component formed on the surface layer having the crystalline zirconia.

8. A hard tissue repairing material obtainable by a process comprising the steps of preparing a base material; coating the base material with a zirconia sol; and crystallizing said zirconia sol.

9. A process for producing a hard tissue repairing material, said process comprising the steps of:

(a) preparing a base material;

(b) coating the base material with a zirconia sol; and (c) crystallizing the zirconia sol.

10. The process for producing a hard tissue repairing material according to claim 9, wherein the step of crystallizing the zirconia sol is carried out by heating the zirconia sol at a temperature ranging from 500° C. to 800° C.

11. The process for producing a hard tissue repairing material according to claim 9, said process further comprising, after the step (b), the steps of:

(d) heating the base material having the zirconia sol on the surface, whereby the diffusing layer having at least an element of the base material and at least an element of the zirconia sol is formed on the base material; and (e) coating the diffusing layer with a zirconia sol;

wherein, at the step (c), the zirconia sol on the diffusing layer is crystallized, whereby the surface layer having a crystalline zirconia is formed, and a middle layer between the base material and the surface layer is formed by the diffusion layer.

12. The process for producing a hard tissue repairing material according to claim 9, wherein the base material includes a hydrophilic group.

13. The process for producing a hard tissue repairing material according to claim 9, further including the step of soaking the base material in an alkaline aqueous solution or an acid aqueous solution after the step of preparing the base material, whereby the base material has included a hydrophilic group.

14. The process for producing a hard tissue repairing material according to claim 9, wherein the zirconia sol includes at least an ionic component selected from a group consisting of calcium ion, sodium ion, potassium ion, and phosphate ions.

15. The process for producing a hard tissue repairing material according to claim 9, further comprising the step of soaking the base material in a molten salt containing at least an ionic component selected from a group consisting of calcium ion, sodium ion, potassium ion, and phosphate ions, after the step of crystallizing the zirconia sol.

16. The process for producing a hard tissue repairing material according to claim 9, further comprising the step of soaking the base material in an aqueous solution containing at least an ionic component selected from a group consisting of calcium ion, sodium ion, potassium ion, and phosphate ions, after the step of crystallizing the zirconia sol.

17. The process for producing a hard tissue repairing material according to claim 9, further comprising the last step of soaking the base material including the surface layer having the crystalline zirconia in the simulated body fluid with ion concentrations nearly equal to those of human body fluid.

* * * * *